(12) United States Patent
Sendowski et al.

(10) Patent No.: US 6,808,149 B1
(45) Date of Patent: Oct. 26, 2004

(54) HANDS-FREE WALL MOUNTED BOTTLE HOLDER

(76) Inventors: Merav Sendowski, 229 C Kenville Rd., Buffalo, NY (US) 14215; Ilan Sendowski, 19108 Lull St., Reseda, CA (US) 91335; Amikm Glass, 10500 Keokuk Ave., Chatsworth, CA (US) 91311

( * ) Notice: Subject to any disclaimer, the term of this patent is extended or adjusted under 35 U.S.C. 154(b) by 0 days.

(21) Appl. No.: 10/774,946

(22) Filed: Feb. 7, 2004

(51) Int. Cl.⁷ .......................... A47K 1/08; A47B 73/00
(52) U.S. Cl. ................. 248/311.3; 248/312; 211/75; 222/181.2; 222/181.3
(58) Field of Search .................. 248/311.2, 311.3, 248/312; 222/181.2, 181.3, 185.1, 181.1; 211/74, 75

(56) References Cited

U.S. PATENT DOCUMENTS

| | | | | |
|---|---|---|---|---|
| 1,633,083 A | * | 6/1927 | Fite, Jr. ..................... 248/105 |
| 1,829,353 A | * | 10/1931 | Hogan ......................... 248/143 |
| 2,200,024 A | * | 5/1940 | De Sipio et al. ........... 222/162 |
| 2,252,260 A | * | 8/1941 | Jones ........................ 248/311.2 |
| 2,678,755 A | * | 5/1954 | Buras, Jr. ................... 222/103 |
| 3,762,673 A | | 10/1973 | Kosovsky |
| 3,814,293 A | * | 6/1974 | Daves ......................... 222/173 |
| 3,872,868 A | * | 3/1975 | Kline .......................... 604/403 |
| 3,982,716 A | | 9/1976 | Trees |
| 4,278,225 A | * | 7/1981 | Phelps ..................... 248/311.3 |
| 4,461,445 A | * | 7/1984 | Williamson et al. ......... 248/551 |
| 4,475,915 A | | 10/1984 | Sloane |
| 4,489,766 A | | 12/1984 | Montada |
| 4,784,360 A | * | 11/1988 | Mok .......................... 248/313 |
| 4,957,260 A | * | 9/1990 | Shelley .................... 248/311.3 |
| 5,002,246 A | * | 3/1991 | Chaffin et al. .............. 248/153 |
| 5,056,744 A | | 10/1991 | Ludwig |
| 5,749,490 A | * | 5/1998 | Keicher ...................... 220/481 |

FOREIGN PATENT DOCUMENTS

GB    1414403    * 11/1975   .............. 248/311.3

* cited by examiner

Primary Examiner—Anita King
Assistant Examiner—Jon Szumny
(74) Attorney, Agent, or Firm—Ilan Sendowski

(57) ABSTRACT

A Hands-Free Wall Mounted Bottle Holder apparatus enables a practitioner to prepare in advance a set of medicine bottles required during a medical procedure, mount the bottles in the proper position on a flat solid surface in an ergonomically preferred secure and locked condition, and then withdraw medicines in sterile fashion during the procedure without the assistance of another person.

12 Claims, 13 Drawing Sheets

General view of assembled apparatus.

Neck holder with a groove to hold different size bottles

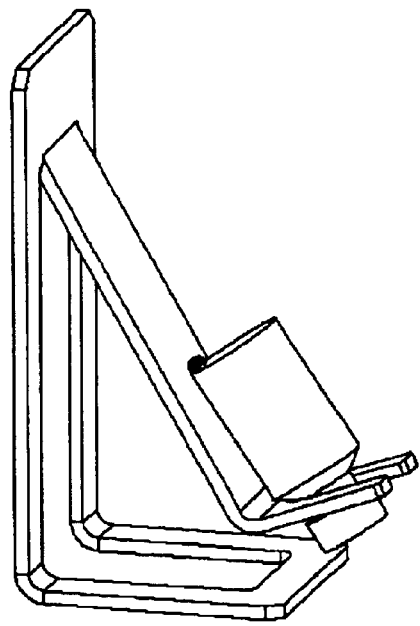
Fig. 1 General view of assembled apparatus.

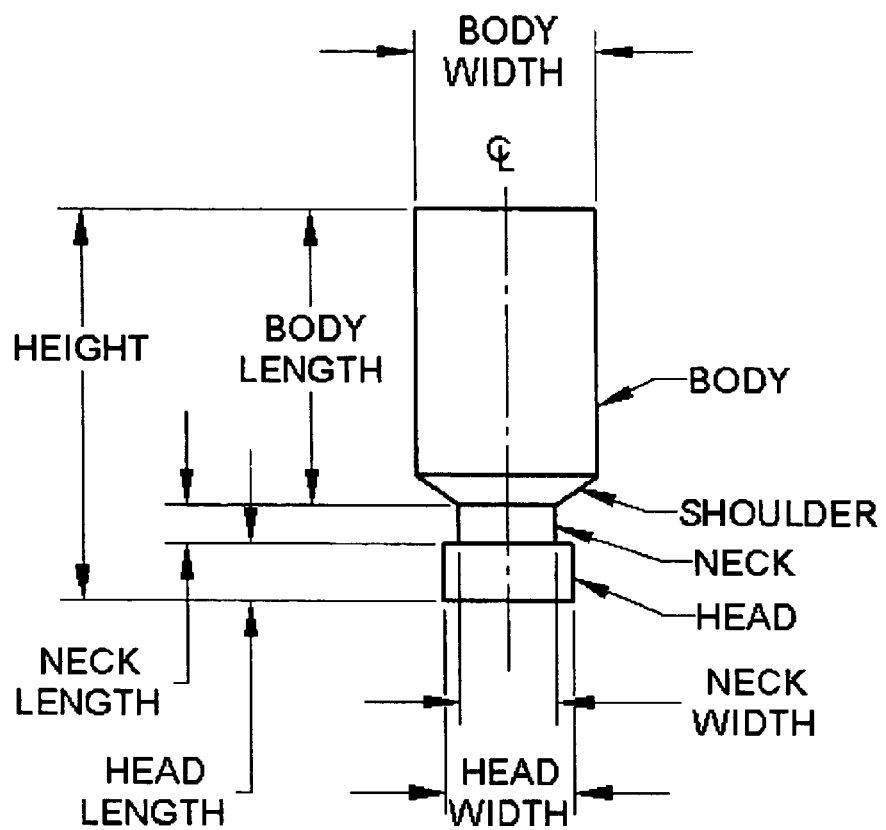
FIG. 2    General view of a bottle with its main dimensions.

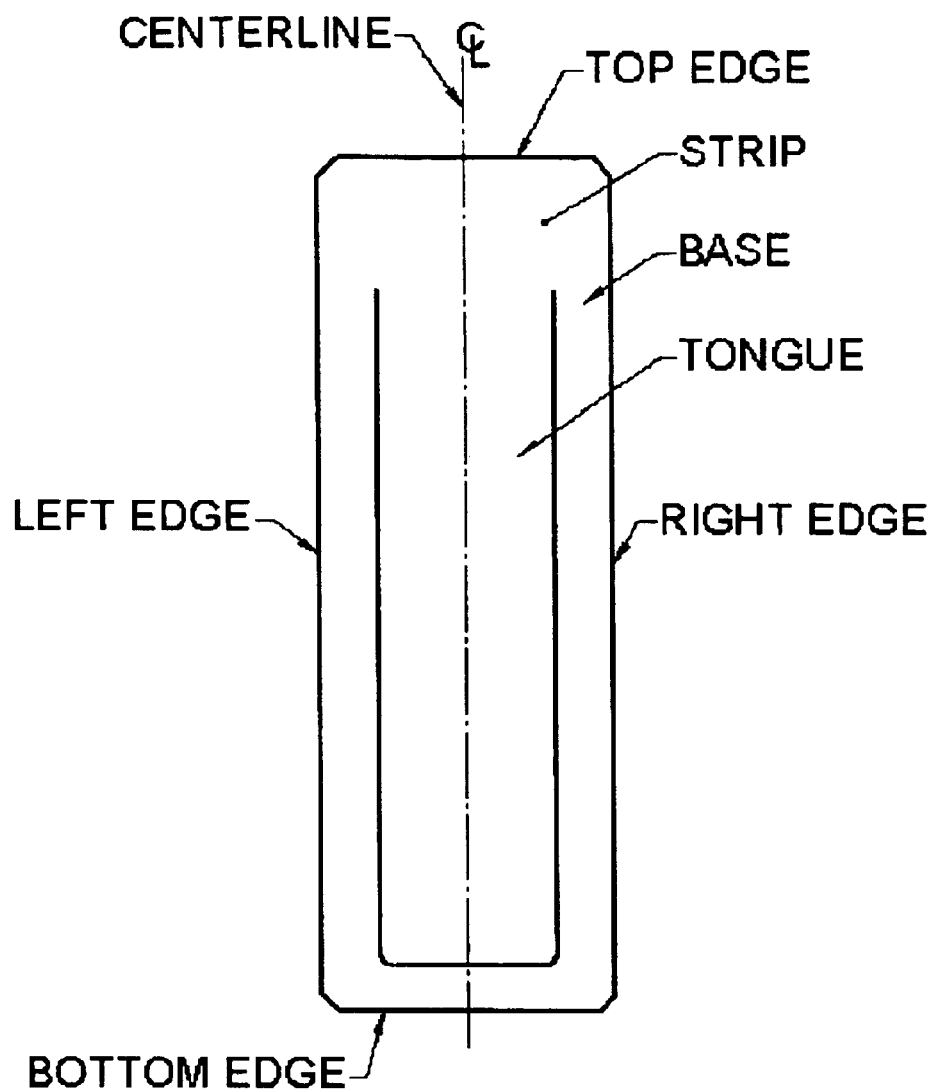
FIG. 3    Front view of the strip with the marking cuts.

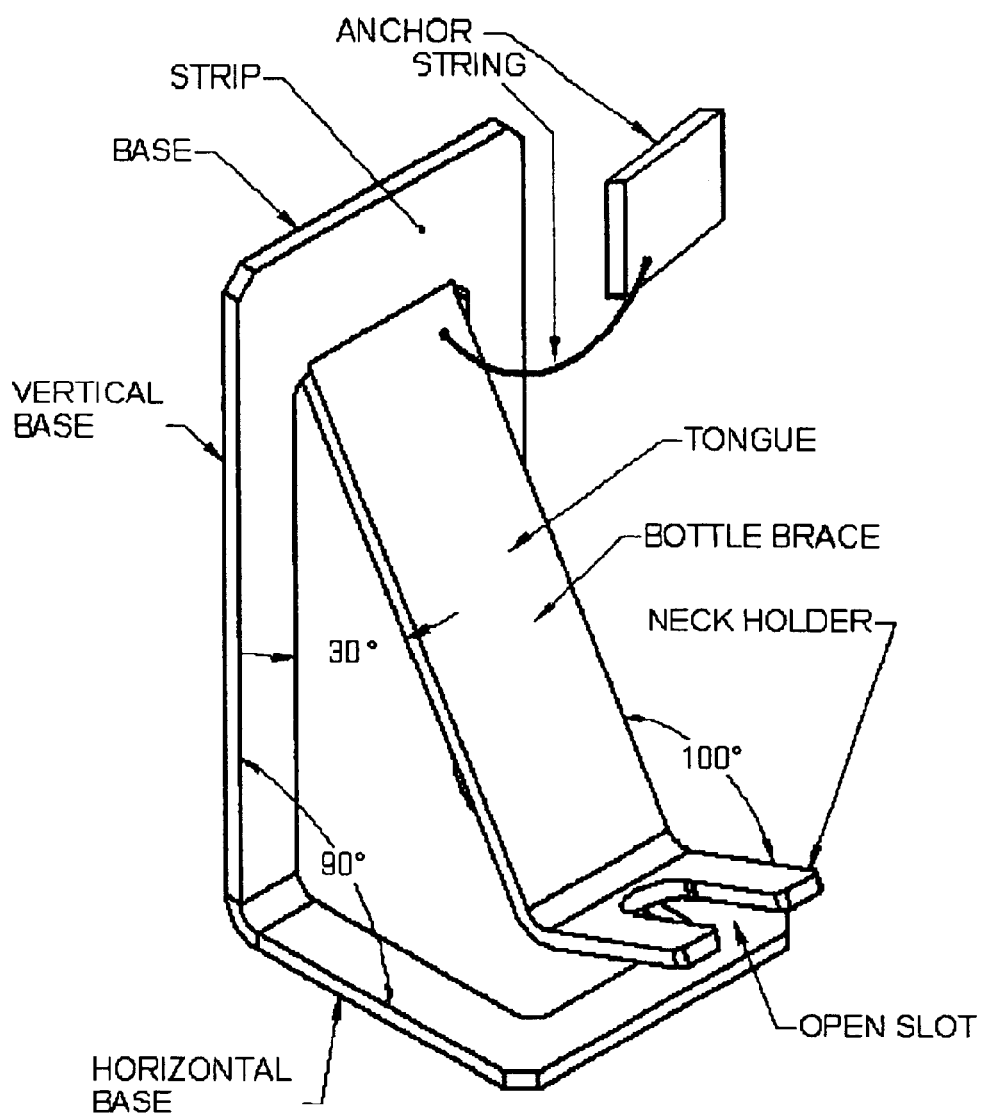
FIG. 4    General view of the apparatus with the main sections.

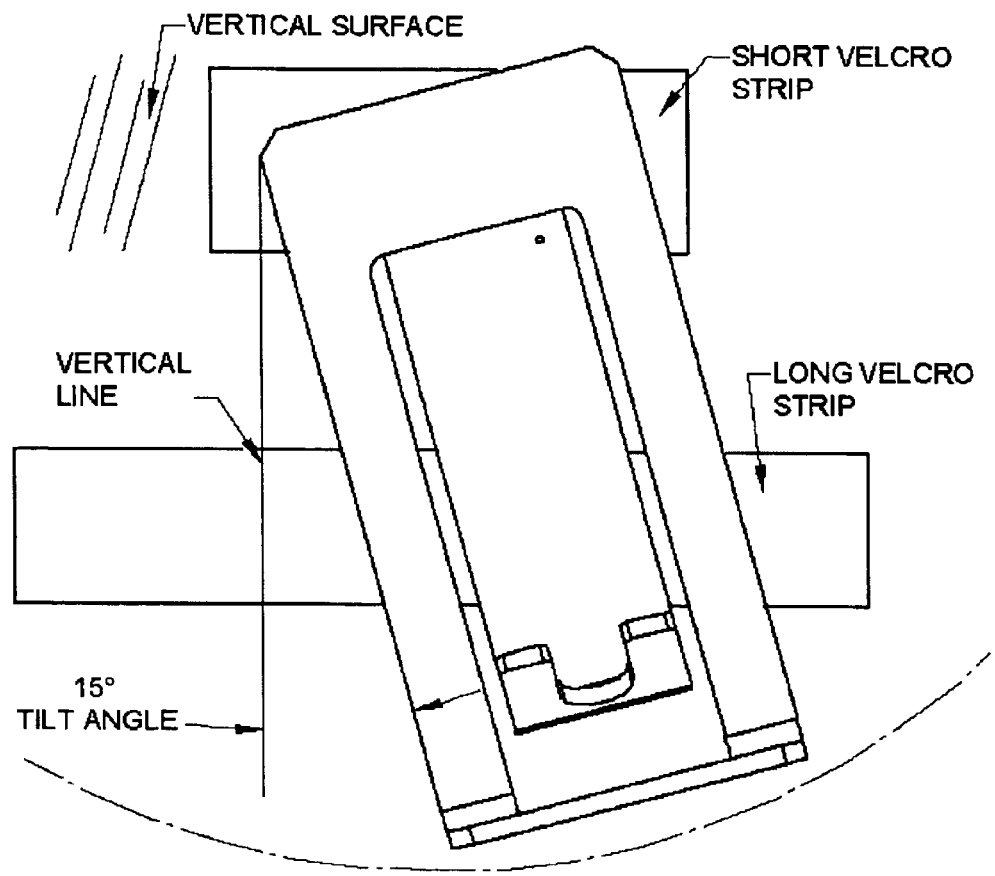
FIG. 5　　Front view of vertical surface mount with a tilt angle.

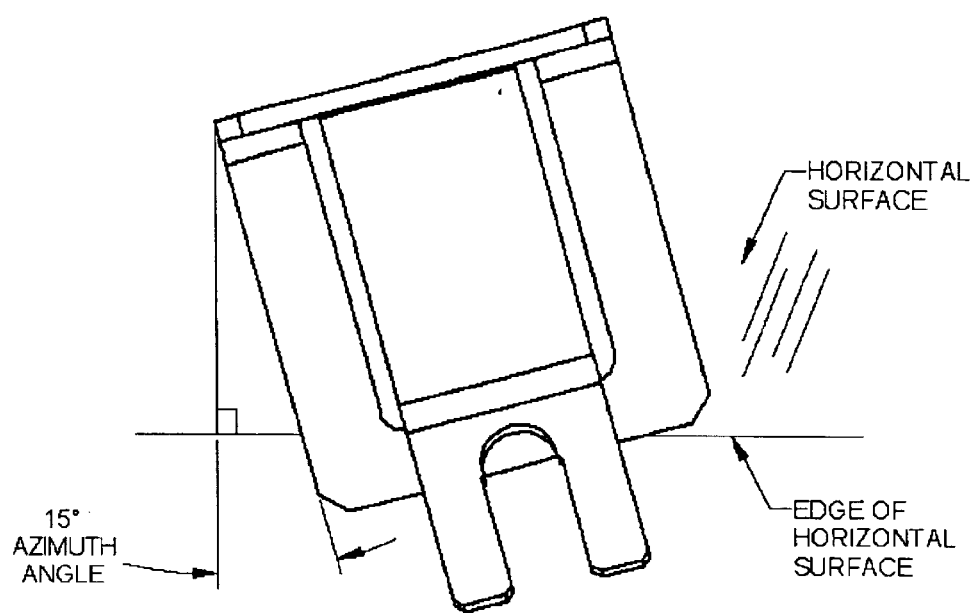
FIG. 6  Top view of horizontal surface mount with an azimuth angle.

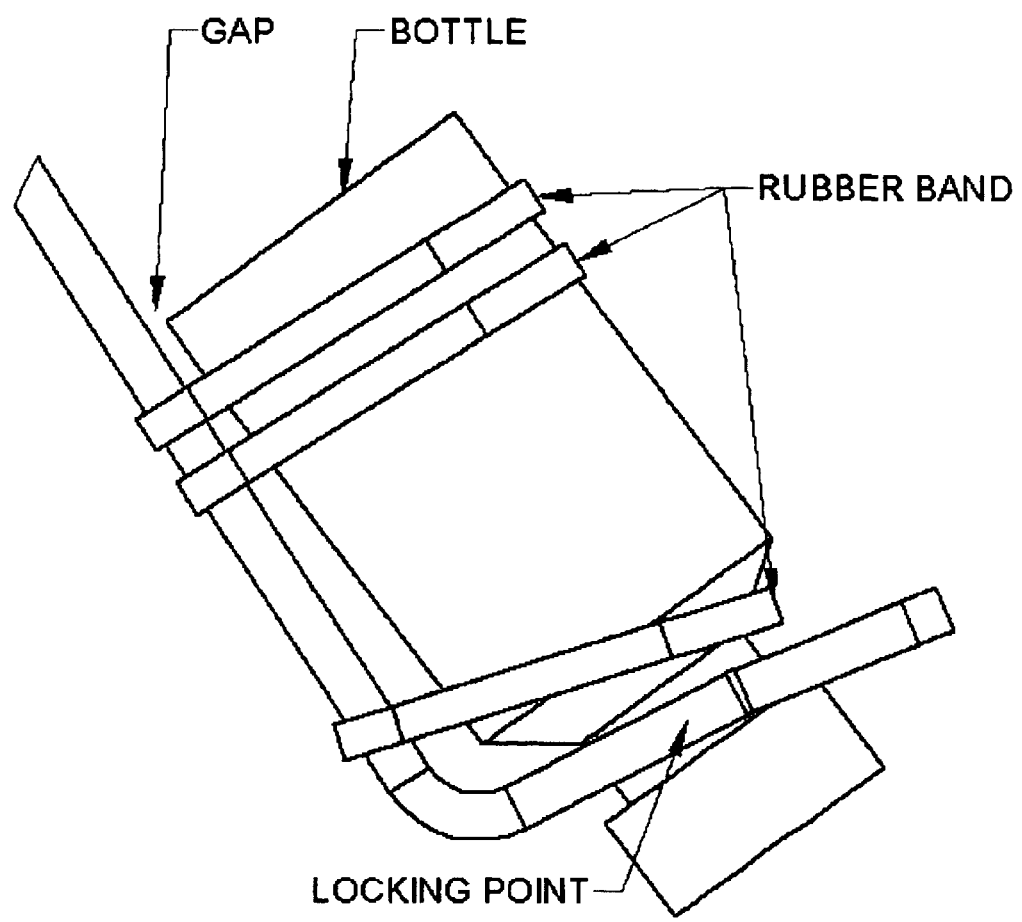
FIG. 7　　Fastening device using rubber bands and locking point of apparatus.

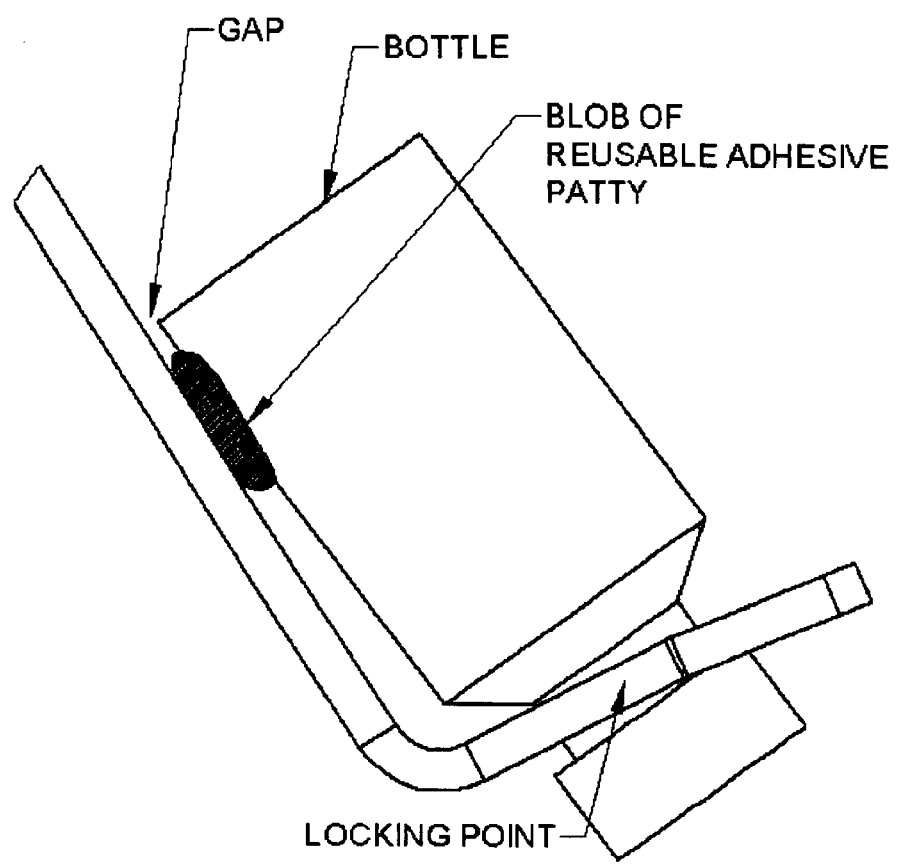
FIG. 8 Fastening device using a blob of reusable adhesive patty.

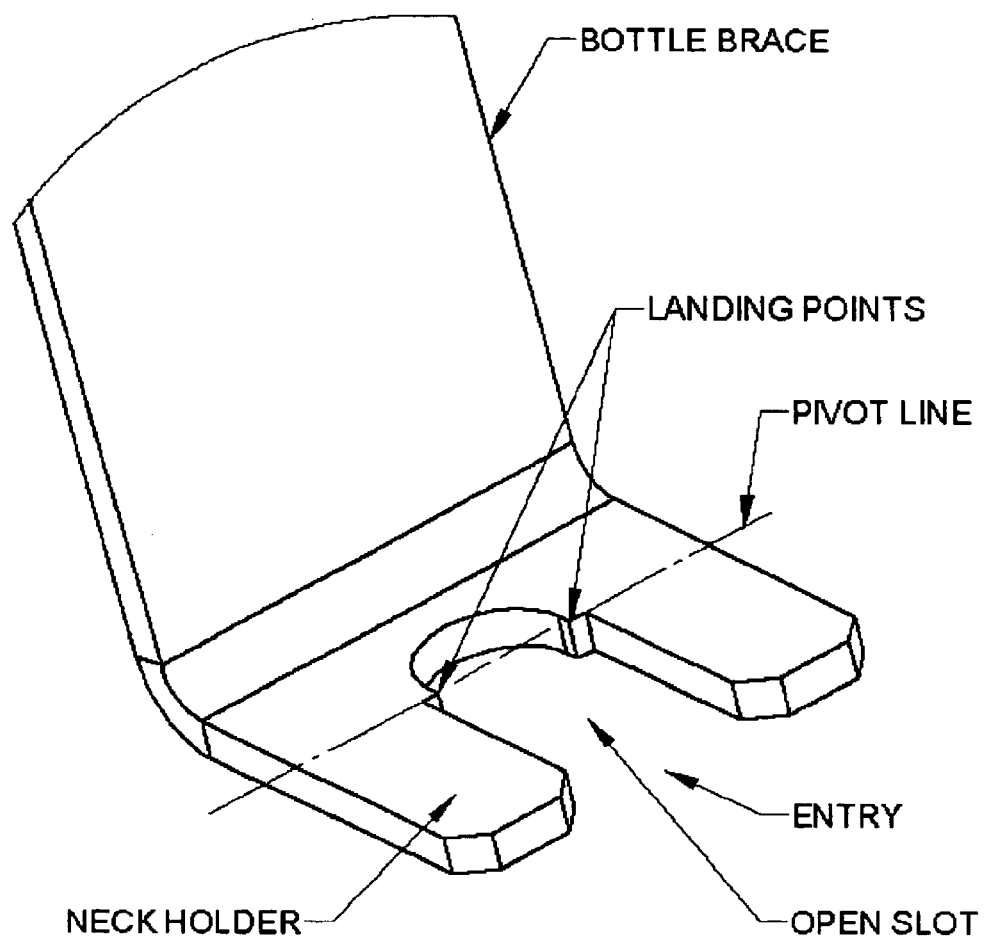
Fig. 9     Landing points and pivot line for the locking point

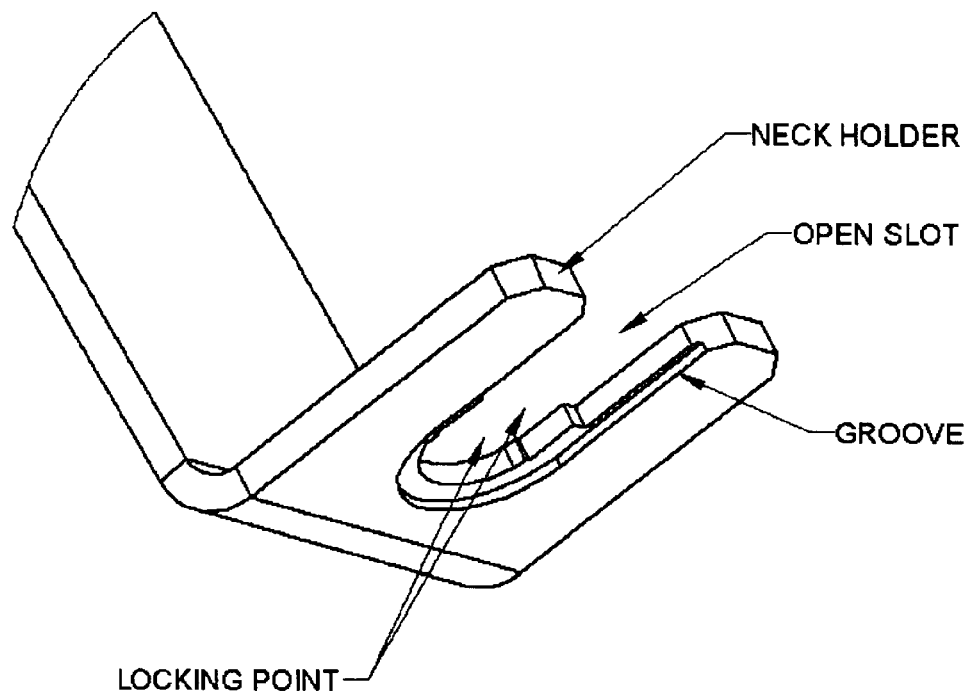
Fig. 10  Neck holder with a groove to hold different size bottles

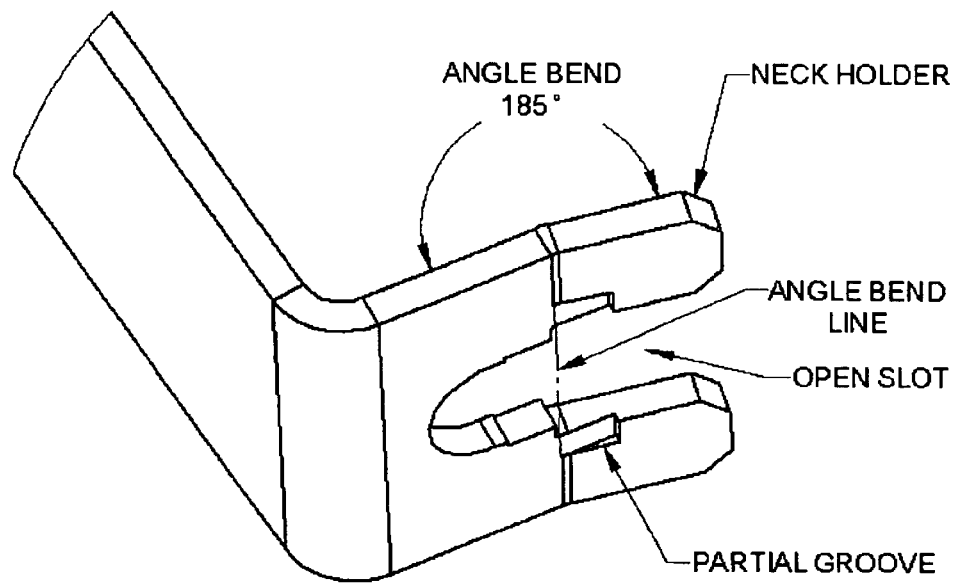
Fig. 11 Neck holder with an angle bend and a partial groove to hold different size bottles

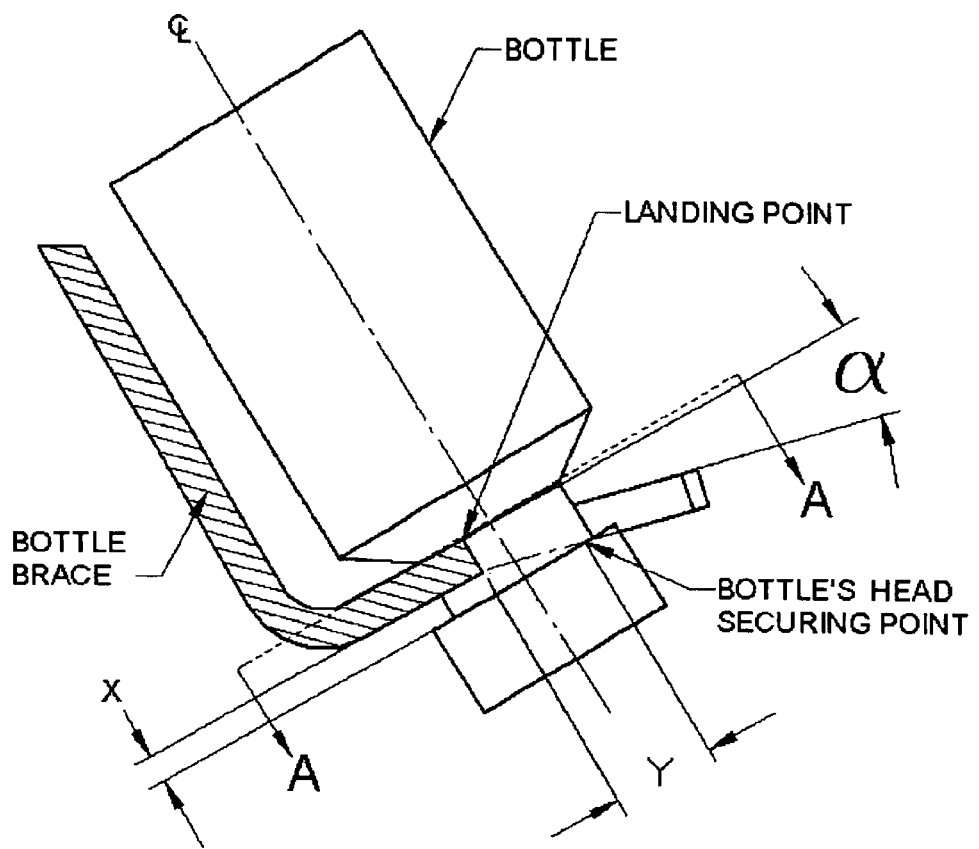
FIG. 12 A cross section of the neck holder with an angle bend and estimate of the α angle.

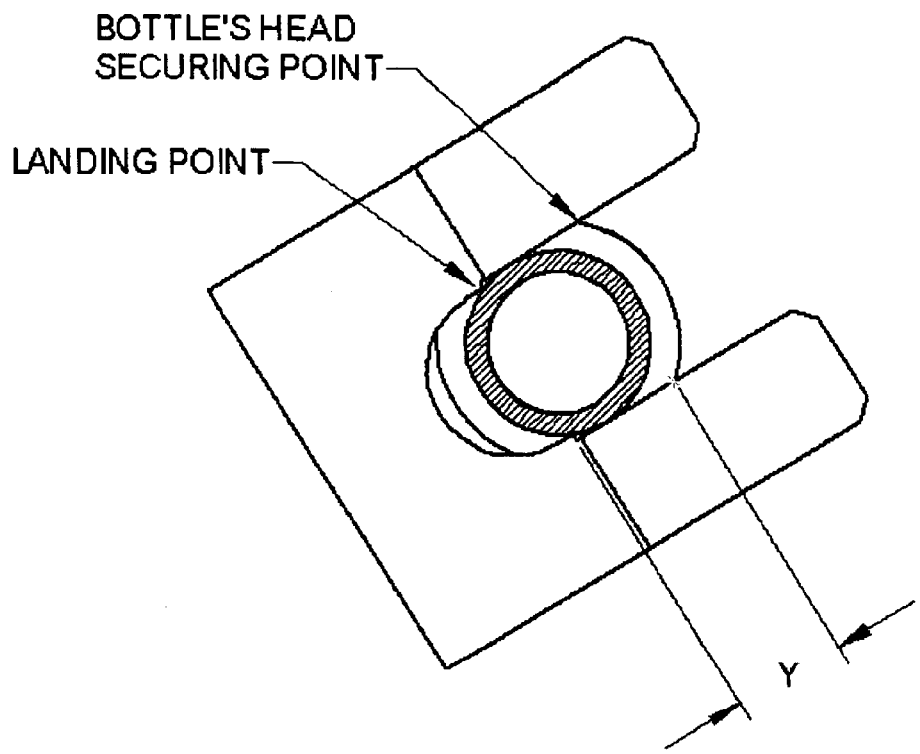
FIG. 13 A top view of a cross section of the neck holder with an angle bend and estimate of the α angle. View A-A in FIG. 12.

HANDS-FREE WALL MOUNTED BOTTLE HOLDER

BACKGROUND OF THE INVENTION

Extracting liquid from a bottle into a syringe is a complex operation. Physicians need to maintain a sterile field during certain procedures, necessitating the use of sterile gloves and sterile equipment. The septum of certain multi-use bottles is sterile, while the exterior surface of the same multi-use bottles is not sterile. Handling the non-sterile exterior surface of bottles during a sterile procedure requires the assistance of another person or use of multiple layers of gloves. These options are expensive, cumbersome and time-consuming. An apparatus that holds the bottle in a proper position eliminates these expensive options and enables the practitioner to use both hands in a sterile fashion without additional assistance.

BRIEF SUMMARY OF THE INVENTION

A Hands-Free Wall Mounted Bottle Holder positions a bottle upside-down in a secured and locked condition. For improved ergonomics, based on individual practitioner preference, the bottle is held at a forward angle toward the practitioner and at either a right tilt or left tilt angle from the vertical.

DESCRIPTION OF THE DRAWINGS

FIG. 1 General view of an assembled apparatus.

FIG. 2 General view of a bottle with its main dimensions.

FIG. 3 Front view of the strip with the marking cuts.

FIG. 4 General view of the apparatus with the main sections.

FIG. 5 Front view of vertical surface mount with a tilt angle.

FIG. 6 Top view of horizontal surface mount with an azimuth angle.

FIG. 7 Fastening device using rubber bands and locking point of apparatus.

FIG. 8 Fastening device using a blob of reusable adhesive patty.

FIG. 9 Landing points and pivot line for the locking point.

FIG. 10 Neck holder with a groove to hold different size bottles.

FIG. 11 Neck holder with an angle bend and a partial groove to hold different size bottles.

FIG. 12 A cross section of the neck holder with an angle bend and estimate of the α angle.

FIG. 13 A top view of a cross section of the neck holder with an angle bend and estimate of the α angle. View A—A in FIG. 12.

DETAILED DESCRIPTION

A Hands-Free Wall Mounted Bottle Holder apparatus consists of a solid, flexible or rigid material that is cut or made into a long rectangular shape strip. (FIG. 3) The strip can be made of various materials such as plastic, metal, glass, wood or stone. The apparatus is designed to hold a bottle that is built of 3 main parts: a head, a neck and a body which includes a shoulder transition to the neck. The bottle body and head are wider than the bottle's neck. (FIG. 2) Through the center of each bottle part, from top to bottom, runs a centerline. The strip's length is about 3 to 7 times the height of the bottle or about 10 to 20 centimeters long. The strip's width is about 2 centimeters wider than the width of the bottle's body, about 6 centimeters wide. The thickness of the strip is as thick as required, based on the material used, to insure a solid secure structure, about 2 millimeters. The strip, mounted flat on a vertical surface such as a wall, has a front surface facing forward and a rear surface facing the vertical surface. Left and right are defined as the left and right of a practitioner looking at the strip from the front. The strip has a top edge and a bottom edge that are the width of the strip and a left edge and a right edge that are the length of the strip. The strip has a centerline going from the center of the top edge to the center of the bottom edge. (FIG. 3) The strip is bent several times to create the apparatus. All the bends are perpendicular to the left and right edges and create rectangular sections. When looking at the left edge of the strip, the bends are either clockwise or counter clockwise. The surfaces of all sections of the strip retain their original designation of the strip, as front surface and rear surface of the section regardless of their actual orientation. The edges of all sections of the strip retain their original designation of the strip as top, bottom, left and right edge of the section regardless of their actual orientation. An angle is measured from the front surface of a section before the bend is made to the front surface of the same section after the bend is made. In this apparatus the width of the strip and each of its sections is constant. However, it is possible to design the apparatus such that each section has a different width or a variable width. The strip is divided into 2 main sections:

1. A first part of the strip is a tongue. The tongue holds the bottle upside down, leaning forward, and at a tilt angle to the right or the left for improved ergonomic use.
2. A second part of the strip is a base. The rear surface of the base is used to attach the apparatus to a smooth flat vertical surface such as a wall, door, cabinet's door, window or mirror or to a smooth flat horizontal surface such as the top surface of a table, cabinet, chair or shelf.

The tongue is created as follows:

1. Marking a rectangle on the strip symmetrical to the centerline of the strip. The top edge of the rectangle is about 1 to 5 centimeters below the top edge of the strip. The bottom edge of the rectangle is about 0.7 to 3 centimeters above the bottom edge of the strip. The left edge of the rectangle is about 0.7 to 1.5 centimeters medial to the left edge of the strip. The right edge of the rectangle is about 0.7 to 1.5 centimeters medial to the right edge of the strip.
2. Cutting, all the way through, the left, right and bottom marked edges of the rectangle.
3. Bending the rectangle, relative to the strip, 15 to 60 degrees counter clockwise, preferably 30 degrees, along the top edge of the rectangle that is still connected to the strip, to create the tongue.

The base is the part of the strip that remains after creating the tongue.

The base is divided into two sections:

1. A vertical base for attaching the apparatus to the smooth flat vertical solid surface.
2. A horizontal base for attaching the apparatus to the smooth flat horizontal solid surface.

The horizontal base is created by bending counter clockwise the bottom 25 to 50 percent of the base's length at an angle of 70 to 90 degrees, preferably 90 degrees. The vertical base is the top 50 to 75 percent of the base's length that remains.

The tongue is divided into two sections:
1. A bottle brace section that is about 10 centimeters long starting from the top edge of the tongue. The bottle brace holds the bottle and pulls the bottle's body using a fastening device.
2. A neck holder section that is about 3 to 5 centimeters long starting from the bottom edge of the bottle brace and extending until the bottom edge of the tongue. The neck holder is bent counter clockwise at an angle of 70 to 90 degrees, preferably 80 degrees. The neck holder holds the neck of the bottle upside down and locks the head of the bottle to its structure as the result of a force created by the fastening device on the bottle's body.

As a rule of thumb the length of the bottle brace should be longer than the height of the bottle and the length of the neck holder should be longer than the width of the bottle's body. All the main parts of the apparatus are shown in FIG. 4.

The main purpose of the neck holder is to provide a locking point, wherein the bottle is secured inside the apparatus in an upside down position while the bottle's head is pointing down. At the approximate center of the bottom edge of the tongue, in the neck holder section, there is an open slot extending from the front surface to the rear surface of the neck holder. The open slot has an entry at the center of the bottom edge of the tongue and extends toward the bottle brace section along the strip's centerline in the neck holder, until the locking point. The width of the open slot is slightly wider than the width of the bottle's neck, but narrower than the width of the bottle's head and body. The edges of the open slot are equidistant from the left and right edges of the neck holder. The thickness of the neck holder is slightly shorter than the length of the bottle's neck. If the thickness of the strip exceeds the length of the bottle's neck, a groove can be cut on the rear surface of the neck holder at a width of the bottle's head width, such that the neck holder thickness around the open slot is slightly shorter than the length of the bottle's neck. Thus, the groove enables the bottle's neck to enter the open slot and travel along the open slot all the way to the locking point. (FIG. 10)

The bottle's neck is inserted upside down through the entry of the open slot into the open slot such that the body of the bottle is above the front surface of the neck holder and the bottle's head is under the rear surface of the neck holder. The bottle travels through the entry of the open slot toward the bottle brace with its centerline parallel to the bottle brace front surface. The distance between the bottle brace front surface and the bottle body is called a gap. When the gap measures 1 to 20 millimeters the bottle has arrived at the locking point. (FIG. 7) At the locking point the open slot width is slightly narrowed on both its left and right sides such that the bottle's neck cannot proceed any further toward the bottle brace. The narrowed open slot continues for a length of half the width of the bottle's neck to accommodate the bottle's neck. The narrowing of the open slot creates two landing points where the bottle's shoulder touches the front surface of the neck holder. The line between these two landing points is a pivot line. (FIG. 9) When the bottle's neck is positioned in the locking point and the bottle's body is pulled toward the bottle brace, the bottle tilts on the pivot line toward the bottle brace. The bottle continues to tilt on the pivot line until the bottle's head touches the rear surface of the neck holder at two bottle's head securing points located on both sides of the rear of the open slot. The gap is 0.5 to 20 millimeters when the bottle is secured in the locking point. If the bottle's body is touching the bottle brace and there is no gap, and the bottle's head did not arrive at the bottle's head securing point, then an angle bend in the neck holder is required. The angle bend is made along an angle bend line. The angle bend line is the line between two points on the rear surface of the neck holder where the open slot narrows down going from the left edge of the neck holder to the right edge of the neck holder. The angle bend is bent clockwise at an angle of α degrees such that the neck holder front surface after the angle bend is at an angle of about (90+α) degrees from the bottle brace. (FIGS. 12, 13) The α angle is estimated as follows:

$$\alpha = \tan^{-1}\left(\frac{\text{length of bottle's neck} - \text{thickness of the strip}}{\sim \frac{1}{2} \text{ width of bottle's head}}\right) = \tan^{-1}\left(\frac{X}{Y}\right)$$

The α angle calculation is only an estimate because it depends on the delta between the width of the open slot and the width of the bottle's neck, the width of the open slot at the landing points, the ratio between the width of the bottle's neck and the width of the bottle's head, and the cross section shape of the bottle neck and head as a circle, or square or otherwise. If the neck holder front surface already had an actual angle greater than 90 degrees to the bottle brace front surface, then the required bending of the angle bend is only the difference between the estimated α and the actual angle before the angle bend is made. To protect the bottle from an accidental touch that might dislodge the bottle from the apparatus, the length of the neck holder should extend some 5 millimeters beyond the bottle's head securing point toward the bottom edge of the neck holder.

If several different sized bottles are to be used on the same apparatus, but not at the same time, and the largest bottle's neck length is shorter than the thickness of the strip, then the following neck holder is devised. It can be assumed that a large bottle has a wider body, neck, and head as well as longer neck than a smaller bottle. The bottles are arranged from the largest to the smallest and one bottle at a time is selected. The width of the open slot must be able to accommodate the varying widths of the bottles' necks, starting from the largest to the smallest. To achieve this flexibility a set of grooves are designed on the rear surface of the neck holder. (FIG. 10) Each groove creates the proper depth for each bottle, all around the open slot. The depth of the groove is the delta between the thickness of the strip and the length of the neck of the bottle that is using that groove. The width of the groove is the width of the bottle's head that is using that groove. The locking point requirements for each bottle should be satisfied for a secure and locked operation. The length of the neck holder should be long enough to accommodate the largest bottle.

If several different sized bottles are to be used on the same apparatus, but not at the same time, and the smallest bottle's neck length is longer than the thickness of the strip, then the following neck holder is devised. It can be assumed that a large bottle has a wider body, neck, and head as well as longer neck than a smaller bottle. The bottles are arranged from the largest to the smallest and one bottle at a time is selected. The neck holder is built and bent in the a angle as if it is made for the selected bottle only, starting from the smallest to the largest bottle. When all the angle bends are formed, a larger bottle may interfere with a smaller bottle at the bottle's head securing point of the smaller bottle because of the angle bend. To resolve this problem for the smaller bottle, a partial groove is made in the rear surface of the neck holder from the angle bend line of the larger bottle extending toward the entry. The partial groove is symmetrical to the strip centerline along both edges of the open slot. The width of the partial groove is slightly larger than the width of the smaller bottle's head. The partial groove ends at a distance of half the width of the smaller bottle's head plus 5 millimeters, from the angle bend line of the smaller bottle. In this way the smaller bottle retains a smooth continuous rear surface on the neck holder, as was present before the angle bend was made for the larger bottle, and the rear surface of the neck holder for the smaller bottle is on one flat plane surface. (FIG. 11)

The methods of creating locking points with a groove or an angle bend can be used together in the same apparatus to accommodate various bottle sizes. It is possible to select a set of bottles sizes that cannot operate on the same apparatus and a different apparatus should be built for each subset.

The fastening device can be made of a rubber band or a Velcro strip or a blob of reusable adhesive putty. The fastening device encompasses the bottle brace section and the upper part of the bottle's body when it is mounted upside down. The fastening device holds and pulls the bottle's body toward the bottle brace. (FIG. 7) If a rubber band is used as a fastening device, it is preferable to use two or more rubber bands together to prevent the effects of accidental breakage of the fastening device during the procedure. The chance of two rubber bands breaking simultaneously is very small. In addition, to prevent accidental slippage of the head of the bottle out of the neck holder, another rubber band is used to pull the bottle's neck to the bottle brace and to secure the bottle's neck in the locking point. If a blob of reusable adhesive is used, the gap should be about 0.5 to 1 millimeter when the bottle is at the locking point. The blob of reusable adhesive has a thickness of about 1 to 2 millimeters and is spread 0.1 to 1 centimeters, preferably about 5 millimeters wide, on the front surface of the bottle brace along the centerline between the bottle's body and the bottle brace. The bottle's body is pressed into the blob of reusable adhesive to create the locking point and secure the bottle to the neck holder. Pulling out the bottle releases the bottle from the blob of reusable adhesive and from the apparatus. (FIG. 8)

The rear surface of the vertical base can be attached to a solid structure using screws, nails or glue as a permanent attachment, or Velcro sheets or reusable adhesive for a temporary attachment. When the apparatus is attached to a vertical surface and a bottle is mounted in the locking point of the apparatus, the bottle's head is pointing down toward the floor. For improved ergonomics, the apparatus is mounted at a tilt angle between +/−60 degrees to the right or to the left, based on practitioner's preference. (FIG. 5) A preferred tilt angle is about 15 degrees of a vertical line either to the right or the left. When the rear surface of the horizontal base is attached on top of a horizontal surface, the apparatus is mounted at the edge of the horizontal surface and is set at an angle of between +/−30 degrees in azimuth, based on practitioner's preference for improved ergonomics. A preferred azimuth angle is about 15 degrees either to the right or to the left. (FIG. 6) The apparatus is constructed and mounted in such a way as to create some distance from the solid structure surface and in doing so prevents contact between the practitioner's sterile gloved hand and the solid structure surfaces behind the apparatus.

Using a reusable adhesive or Velcro material to attach the apparatus to a flat solid surface enables the practitioner to adjust the angle to personal preference and remove the apparatus easily for safe keeping and cleaning. When using a Velcro material, it is preferred to use a set of Velcro sheets with glue material on one side of each sheet. The glue side of a first sheet is attached to the rear surface of the vertical base along the edges. The second sheet is cut into two strips: a short Velcro strip and a long Velcro strip. (FIG. 5) The short Velcro strip is about 2 centimeters wide and its length is about 110% of the base's width. The long Velcro strip is about 2 centimeters wide and its length is about the base's length. The glue side of the short Velcro strip is attached to the vertical surface in level, at a desired height from the floor. The glue side of the long Velcro strip is attached to the vertical surface below the short Vertical strip and parallel to the short Velcro strip, at a distance of about 2 to 8 centimeters, preferable 5 centimeters, and about 0.25 to 0.75 of the base's length. The short Velcro strip's center and long Velcro strip's center are along a vertical line. A practitioner selects the tilt angle to mount the apparatus, and attaches the vertical base of the apparatus to the short and long Velcro strips at that tilt angle, such that the top of the vertical base in attached to the short Velcro strip. In this way the practitioner is able to select any desired tilt angle based on the practitioner ergonomic preference within a range of +/−60 degrees of a vertical line. Similar process is done to connect the horizontal base to a solid horizontal surface.

When using a reusable adhesive, the reusable adhesive is shaped into thin cylinders with an approximate 1 millimeter radius and a length of the base edge. The reusable adhesive cylinders are spread on the rear surface along the edges of the vertical base for a vertical surface use, or the reusable adhesive cylinders are spread on the rear surface along the edges of the horizontal base for a horizontal surface use. Spreading the reusable adhesive in the center of the vertical or horizontal bases is of reduced value. By exerting a firm pulling force the apparatus can be dismounted and removed.

Risk of dislodging the apparatus during the procedure exists with use of a non-permanent wall attachment. To prevent such an accident an anchor is used. The anchor is made from material similar to that of the strip or any other solid material, and is about the same thickness as the strip. The rear surface of the anchor is flat and can have any small round or square shape with about a 1-centimeter square area. (FIG. 4) The shape of the front of the anchor is for aesthetic purpose only, and can be used for advertisement or company logo. The rear surface of the anchor is flat. The anchor is connected to the bottle brace with a string or a chain measuring 2 to 20 centimeters. The anchor is connected to the vertical surface with reusable adhesive in such a way that the string or chain hangs loosely. If the apparatus is dislodged from the vertical surface the anchor will prevent the fall, and the apparatus can be remounted to the vertical surface.

The apparatus can be created by use of a mold or cast.

A recommended process is to use the apparatus with a reusable adhesive as a method of connecting the apparatus to flat solid surfaces such as the vertical surface or horizontal surface. The process has the following steps:

1. removing the apparatus from a protective container bag or dismounting the apparatus from the flat solid surface;
2. sliding the bottle's neck with the bottle's head pointing down into the open slot of the neck holder all the way until it reaches the locking point;
3. securing the upper part of the bottle's body to the bottle brace with a blob of reusable adhesive so that the upper part of the bottle's body is pulled toward the bottle brace and the bottle's neck is locked in the neck holder open slot due to rotation of the bottle's body created by the fastening device.
4. cutting two or more thin strips of reusable adhesive patty, and attaching the reusable adhesive strips to the rear surface of the vertical base or horizontal base, at the top, bottom, left and right edges of the base section;
5. removing the metal protecting cover off the bottle septum and preparing the bottle for the procedure;
6. attaching the apparatus with the bottle mounted, on a clean reasonably smooth flat solid surface at the desired height and preferred tilt or azimuth angle;
7. attaching the safety anchor to the flat solid surface using the reusable adhesive;
8. subjecting the apparatus to some pressure to verify proper attachment to the flat solid surface;

9. cleaning the bottle head;
10. performing the procedure;
11. removing the bottle;
12. dismounting the apparatus and the anchor from the vertical surface;
13. cleaning the vertical surface from residual of the reusable adhesive;
14. storing the apparatus in a protective container;

If the apparatus is mounted permanently on the flat solid surface there is no need to perform the steps related to dismounting or mounting the apparatus on the flat solid surface or application of the reusable adhesive on the rear surface of the vertical base or horizontal base. Perform steps 2, 3, 5, 9, 10, and 11 only.

We claim:

1. A hands-free wall mounted bottle holder apparatus, for mounting a bottle that comprises: a body, a neck and a head to a flat solid surface, comprising:
   a base, for connecting the apparatus to the flat solid surface; and
   a tongue, that has a root and a free far end, and the tongue's root is connected to the base, comprising:
      a bottle brace, that starts from the tongue's root, and
      a neck holder, for holding the bottle's neck securely in a locking point, with a first edge connecting to the bottle brace at a base angle of about 90 to 120 degrees, and a second edge, which is the tongue's free far end, which remains unattached; and
   a fastening device, for pulling and holding the bottle's body toward the bottle brace and locking the bottle in the locking point; and
   wherein the neck holder has an open slot at the second edge, extending toward the bottle brace at a width adapted to be slightly slightly larger than the width of the bottle's neck until the locking point, located at a distance of about half of the bottle's body width from the bottle brace, wherein the open slot width adapted to narrow down to less than the width of the bottle's neck, creating two landing points, and the open slot adapted to extend toward the bottle brace an additional distance of about half the width of the bottle's neck; and
   wherein the locking point is created by adjusting the base angle and the distance between the landing points such that when the bottle's neck is inserted upside down into the open slot and reaches the landing points, and the bottle's body is pulled toward the bottle brace by the fastening device, the following conditions exist:
      the bottle's body touches the two landing points and turns on a pivot line that connects the two landing points,
      the bottle's head touches the neck holder, and
      the bottle's body has a gap of about 0.5 to 20 millimeters from the bottle brace; and
   a mounting device that connects the base to the flat solid surface such that the bottle's head, at the locking point, is oriented forward and downward 1 to 60 degrees relative to a vertical line, and tilts relative to the vertical line from 60 degrees to the left to 60 degrees to the right, based on ergonomic preferences of a user.

2. An apparatus as in claim 1, where the base further comprises:
   a vertical base section for connecting the apparatus to a flat vertical solid surface; and
   a horizontal base section for connecting the apparatus to a flat horizontal surface and the horizontal base section is connected at an angle of about 70 to 90 degrees, to the vertical base.

3. An apparatus as in claim 1, where the fastening device further comprises:
   1 to 5 rubber band ring(s) adapted to encompass the bottle brace and the bottle's body that pull(s) the bottle's body to the bottle brace.

4. An apparatus as in claim 3, where the fastening device further comprises:
   an additional 1 to 5 rubber band ring(s) adapted to encompass the bottle brace and the bottle's neck that pull(s) the bottle's neck to the bottle brace, for added security.

5. An apparatus as in claim 1, where the fastening device further comprises:
   a blob of reusable adhesive putty spread at a width of about 0.1 to 1 centimeter on the front surface of the bottle brace along the centerline of the bottle brace in front of the bottle's body, and the blob of reusable adhesive fills the gap, and when the bottle's body is pressed into the blob of reusable adhesive the bottle is attached to the bottle brace.

6. An apparatus as in claim 1, where the mounting device further comprises:
   a set of two velcro material sheets with a glue on the back of each velcro sheet, and the glue side of a first velcro sheet is attached to the base, and
   a second velcro sheet further comprises:
      a short velcro strip of about 2 centimeters wide and length of about the base's width, and
      a long velcro strip of about 2 centimeters wide and length of about the base's length;
      wherein the glue side of the short velcro strip is attached to the flat solid surface and the glue side of the long velcro strip is attached to the flat solid surface parallel to the short velcro strip at a distance of about 0.25 to 0.75 of the strip's length.

7. An apparatus as in claim 1, where the mounting device further comprises:
   a reusable adhesive material for attaching the base to the flat solid surface.

8. An apparatus as in claim 7, where the mounting device further comprises:
   an anchor unit uses the reusable adhesive material, for securing the apparatus to the solid surface; and
   a flexible attachment device connects the anchor to the bottle brace.

9. An apparatus as in claim 8, where the flexible attachment device is a string or a chain.

10. An apparatus as in claim 1, wherein the neck holder further comprises:
    a groove all around the open slot that reduces the thickness of the neck holder, enabling the bottle neck to travel along the open slot to the locking point.

11. An apparatus as in claim 1, wherein the neck holder further comprises:
    an angle bend along the pivot line in the neck holder such that bottle's body is touching the neck holder before the angle bend and the bottle's head is touching the neck holder after the angle bend to create the locking point.

12. An apparatus as in claim 11, wherein the neck holder further comprises:
    a partial groove on the rear of the neck holder such that an interference created by a larger bottle angle bend is removed by the partial groove and the neck holder surface around a locking point of a smaller bottle exists as if the angle bend of the larger bottle was not present.

* * * * *